(12) United States Patent
Bisht et al.

(10) Patent No.: US 9,170,203 B2
(45) Date of Patent: Oct. 27, 2015

(54) ENHANCEMENT OF RAMAN SCATTERING

(75) Inventors: Prem Ballabh Bisht, Chennai (IN); Venkata Ramanaiah Dantham, Nellore (IN); Raman Namboodiri, Kozhikode (IN)

(73) Assignee: Indian Institute of Technology Madras, Tamilnadu, Chennai (IN)

( * ) Notice: Subject to any disclaimer, the term of this patent is extended or adjusted under 35 U.S.C. 154(b) by 188 days.

(21) Appl. No.: 13/472,987

(22) Filed: May 16, 2012

(65) Prior Publication Data

US 2013/0308127 A1    Nov. 21, 2013

(51) Int. Cl.
*G01J 3/44* (2006.01)
*G01N 21/65* (2006.01)

(52) U.S. Cl.
CPC ............. *G01N 21/658* (2013.01); *G01J 3/44* (2013.01)

(58) Field of Classification Search
CPC .......................................................... G01J 3/44
USPC ......................................................... 356/301
See application file for complete search history.

(56) References Cited

U.S. PATENT DOCUMENTS

2010/0245816 A1*  9/2010  Shen et al. .................... 356/301
2013/0162990 A1*  6/2013  Kobayashi et al. ........... 356/301

OTHER PUBLICATIONS

"Photonic Nanojets", Journal of Computational and Theoretical Nanoscience, Sep. 2009, vol. 6, 1979-1992 by Heifetz et al (hereinafter Heifetz).*

Kneipp et al., Surface-Enhanced Raman Spectroscopy: a Brief Perspective, Surface-Enhanced Raman Scattering Physics and Applications, Springer Berlin Heidelberg, New York (2006), pp. 1-19.

Kneipp et al., Two-Photon Excited Surface-Enhanced Raman Scattering, Surface-Enhanced Raman Scattering Physics and Applications, Springer Berlin Heidelberg, New York (2006), pp. 1-16.

International Conference on Futuristic Science & Technology in Frontier Areas & 2$^{nd}$ Annual Conference of Indian JSPS Alumni Association, Aug. 5-6, 2011 (Sponsored by Japan Society for the Promotion of Science, Japan).

Chen et al., Photonic nanojet enhancement of backscattering of light by nanoparticles: a potential novel visible-light ultramicroscopy technique, *Optics Express* (Feb. 26, 2004), 12(7):1214-1220.

Dantham et al., Enhancement of Raman scattering by two orders of magnitude using photonic nanojet of a microsphere, *Journal of Applied Physics* (May 16, 2011), 109:103103, pp. 1-4.

Devilez et al., Three-dimensional subwavelength confinement of light with dielectric microspheres, *Optics Express* (Dec. 19, 2008), 17(4):2089-2094.

Futamata, A highly-sensitive measurement system for Raman spectra by a photon counting method, *Meas. Sci. Technol.* (Dec. 1991), 2(12):1 (Abstract).

(Continued)

*Primary Examiner* — Tarifur Chowdhury
*Assistant Examiner* — Jamil Ahmed
(74) *Attorney, Agent, or Firm* — Pepper Hamilton LLP

(57) ABSTRACT

Raman emissions from a sample may be enhanced by using a microsphere to confine the impinging radiation into a photonic nanojet and thereby increase the intensity of the radiation that is striking the sample. The amount of enhancement may be improved by configuring the diameter and refractive index of the microspheres in conjunction with the dispersion and the wavelength of the radiation to increase the intensity of the beam of radiation in the photonic nanojet.

32 Claims, 6 Drawing Sheets

(56) References Cited

OTHER PUBLICATIONS

Heifetz et al., Photonic Nanojets, *J Comput Theor Nanosci.* (Sep. 1, 2009), 6(9):1979-1992.

Priyadarshini, Raman scanning made stronger, *Nature* (Jun. 22, 2011), pp. 1-2.

Yi et al., Enhanced Raman scattering by self-assembled silica spherical microparticles, *J. Appl. Phys.*, (Aug. 23, 2006), 101(063528).

Du, et al., Enhancement of Raman scattering by individual dielectric microspheres, *Journal of Raman Spectroscopy* (2011), 42(2):145-148.

* cited by examiner

ENHANCEMENT OF RAMAN SCATTERING

BACKGROUND

When monochromatic light is directed on a molecule, the light can be either absorbed or scattered. When the light strikes the molecule, the electrons in the molecule will absorb the energy of the light wave and change their energy state. Once this occurs, either the energy is retained by the matter and the light is absorbed, or the electron returns to a lower energy state emitting a photon of light.

If the photon energy is absorbed, the energy from the photon is transformed to other forms of energy, such as heat. In absorption, the frequency of the incoming light wave is at or near the energy levels of the electrons in the matter. However, if the photon is immediately re-emitted, the photon is effectively reflected, or scattered.

When photons are scattered from an atom or molecule, most of the scattered photons have the same kinetic energy (frequency) and wavelength as the incident photons. This type of scattering is elastic scattering and has been named Rayleigh scattering. However, a small fraction of the scattered photons, approximately 1 in 10 million, is scattered by an excitation, wherein the scattered photons have an energy (frequency) that is different from, and usually lower than, that of the incident photons. This type of scattering is inelastic scattering and has been named Raman scattering.

Rayleigh scattered photons generally do not provide any useful information for molecular characterization. Raman scattered photons, on the other hand, are able to provide information about vibrational, rotational and other low frequency transitions in molecules. Detection of the Raman scattering by Raman spectroscopy can therefore be used to study solid, liquid and gaseous samples.

Raman scattering intensity is orders of magnitude weaker than the Rayleigh signal. For example, for gases, the Raman scattering signal is weaker than the Rayleigh signal by a factor of $10^3$. For solids, this difference can be more than $10^6$. The Raman scattering signal can therefore be extremely difficult to detect. It is therefore desirable to enhance the Raman scattering signal to enable trace element detection at lower concentrations, such as parts per billion (ppb) levels.

SUMMARY

Presently disclosed is a method for enhancing Raman scattering signals by means of microspheres which are able to confine the impinging light into photonic nanojets. Depending on the materials being tested, enhancements of at least about 15× and even greater than about 80× may be obtainable upon select configuration of interrelated system parameters.

In an embodiment, a method for enhancing intensity of Raman emissions produced by excitation of a sample with a beam of radiation is disclosed. The method includes providing a sample, a microsphere, and a beam of radiation from a radiation source, wherein the radiation source comprises a lens having a numerical aperture to provide an amount of dispersion to the beam of radiation, and the beam of radiation has at least one wavelength. The microsphere has a portion for receiving the beam of radiation and outputting a photonic nanojet to impinge the sample. The microsphere also has a diameter and a refractive index, with the diameter and refractive index being configured in conjunction with both the dispersion and the at least one wavelength to confine the beam of radiation in the photonic nanojet by an amount sufficient to enhance the Raman emissions by a factor of at least about 15. The microsphere is placed between the radiation source and the sample, and the beam of radiation is directed at the microsphere to impinge the beam of radiation on the microsphere and output the photonic nanojet to impinge the sample, excite the sample, and produce the enhanced Raman emissions.

In an embodiment, a method for enhancing intensity of Raman emissions produced by excitation of a sample with a beam of radiation is disclosed. The method includes placing a microsphere between a radiation source and the sample, the microsphere having a portion for receiving a beam of radiation and outputting a photonic nanojet to impinge the sample, the microsphere being configured in conjunction with at least one characteristic of the beam of radiation to confine the beam of radiation in the photonic nanojet by an amount sufficient to enhance the spectroscopic emissions by a factor of at least about 15. The beam of radiation is directed at the microsphere to impinge the beam of radiation on the microsphere and output the photonic nanojet to impinge the sample, excite the sample, and produce the Raman emissions.

In one embodiment, a method for analyzing a sample by Raman spectroscopy includes scanning the sample with a spectrometer that has a laser source for producing a laser beam of radiation to impinge the sample and produce Raman emissions from the sample, and a detector for receiving the Raman emissions. The method includes placing at least one microsphere on a surface of the sample, wherein the microsphere has a diameter and a portion for receiving the laser beam, confining the laser beam and outputting a photonic nanojet to impinge the sample. The microsphere is configured as a function of at least one characteristic of the laser beam to confine the laser beam in the photonic nanojet by an amount sufficient to enhance the Raman emissions by a factor of at least about 15. The method also includes directing the laser beam at one of microspheres, adjusting at least one of: a dispersion of the laser beam and a distance of the sample from the laser source so that a diameter of the laser beam at the microsphere corresponds to the diameter of the microsphere, and detecting the Raman emissions produced by the photonic nanojet.

DETAILED DESCRIPTION

The energy and wavelength of Raman scattered photons varies based upon the vibrational, rotational and other low frequency transitions in molecules. As a result, the detectable spectrum of the Raman-scattered light from a material is dependent on the molecular constituents present and their state. The spectra produced by various molecules generally include enough differences to allow the spectra to be used for material identification and analysis. Raman spectroscopy may be used to obtain information on the chemical composition and phase transition of materials under investigation. The intensity of the Raman frequency of a molecular vibration is linearly proportional to the concentration of the specific molecule and its cross section.

Raman spectroscopy is therefore usable for analyzing a wide range of materials, including gases, liquids, and solids, and even highly complex materials such as biological organisms and human tissue. Raman spectroscopy has several applications in materials science, nanotechnology, archaeology, forensic science, the biosciences and the pharmaceutical industry. Some examples of types of materials which may be analyzed with Raman spectroscopy include, but are not limited to, pharmaceutical drugs, composites, polymers, gems, semiconductors, carbon compounds, biological tissues, and thin film photovoltaics.

Figure 1:
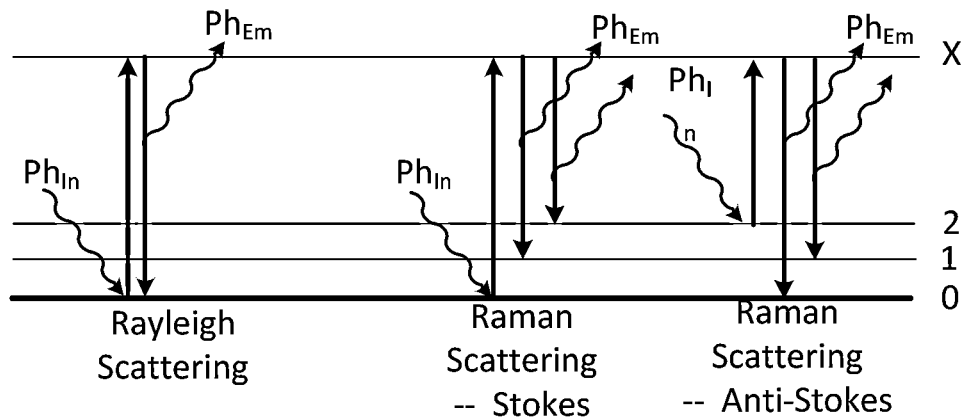
FIG. 1 depicts a general representation of spectroscopic emissions.

As generally depicted in FIG. 1, when electromagnetic radiation is scattered by a molecule, one photon of the incident radiation ($Ph_{In}$) is annihilated and, at the same time, one photon of the scattered radiation ($Ph_{Em}$) is created. Three variations then exist as represented in FIG. 1. In Rayleigh scattering, the energy of the incident photon ($Ph_{In}$) is equal to the energy of the emitted or scattered photon ($Ph_{Em}$), as the excited electron moves from its ground state (0) to a higher energy level (X), and back to the ground state (0).

In Raman scattering, however, the energy of the incident photon ($Ph_{In}$) is different from the energy of the scattered photon ($Ph_{Em}$). In the first and most common scenario (known as Stokes scattering), the incident energy is greater than the energy emitted as an electron is excited from its ground state (0) to a higher energy level (X) but then returns to an alternate level (1 or 2). In the alternate scenario (known as anti-Stokes scattering), the incident energy is less than the energy emitted as an electron is excited from an energy level (2) to a higher energy level (X) but then returns to a lower level (0 or 1).

Since only about 1 in 10 million emissions is a Raman emission, the detection of Raman emissions requires very sophisticated filters to remove undesirable light, such as incident radiation and Rayleigh scattering, and also requires sensitive detectors. Further, due to the small interactive cross sections of the samples being excited, the Raman scattering signal is generally extremely weak.

Figure 2:
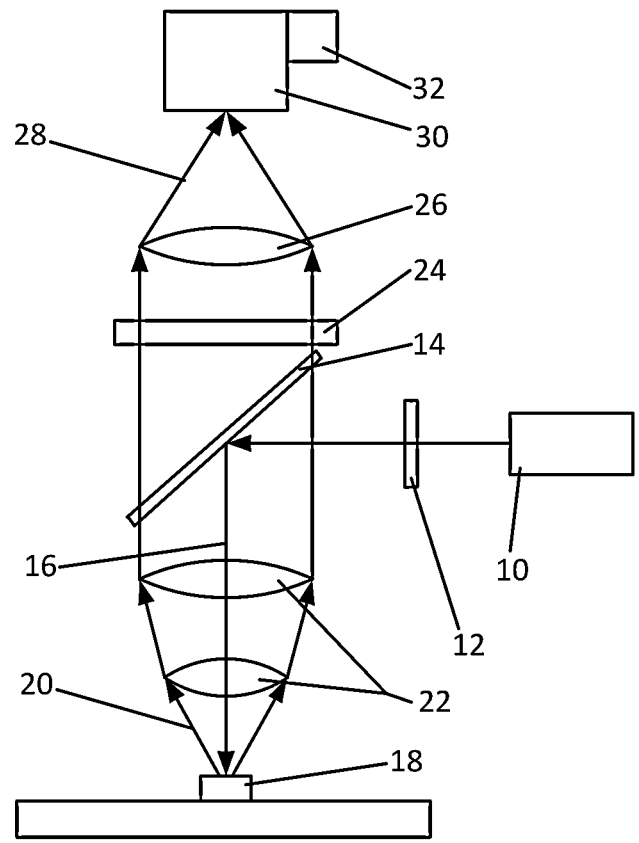
FIG. 2 depicts a basic illustration of a Raman spectroscope usable in an embodiment.

A general representation of a Raman spectroscopy system is depicted in FIG. 2. A high intensity light source 10, which will typically be a laser, provides the impinging light 16 for exciting the electrons. A bandpass filter 12 may be provided for selection of a wavelength of the light. A beam splitter 14 may also be used to allow the system to be more compact. The produced laser beam 16 is directed at the sample 18 and emissions 20 are produced.

An assembly of collection optics 22 may be provided to gather the scattered light emissions 20, and direct the light through filters 24 to remove extraneous light. Additional optics, such as a focusing lens 26 may be used to direct the remaining Raman emissions 28 to a detection system 30 which may include a CCD sensor 32.

To provide increased detectability of Raman scattering, the intensity of the Raman scattering 20 may be increased proportionally to an increase in the intensity of the incident light 16. Raman signals are generally very weak due to the low scattering cross sections. Typical values of Raman scattering cross sections vary between $10^{-30}$ cm$^2$ to $10^{-25}$ cm$^2$ per molecule. The various factors affecting the intensity of the Raman signal ($I_{Raman}$) are, (i) the incident electric field intensity ($I_{incident}$),
(ii) the concentration of the sample (C), and,
(iii) the scattering cross section ($\sigma_R$) of the sample.

and may be equated as follows:

$$I_{Raman} = I_{incident} \times \sigma_R \times C.$$

Therefore, as the $I_{incident}$ is increased, with other factors remaining constant, a greater number of molecules will interact with the available photons. As a result the number of emissions (photons) will increase at the same frequency.

Figure 3:
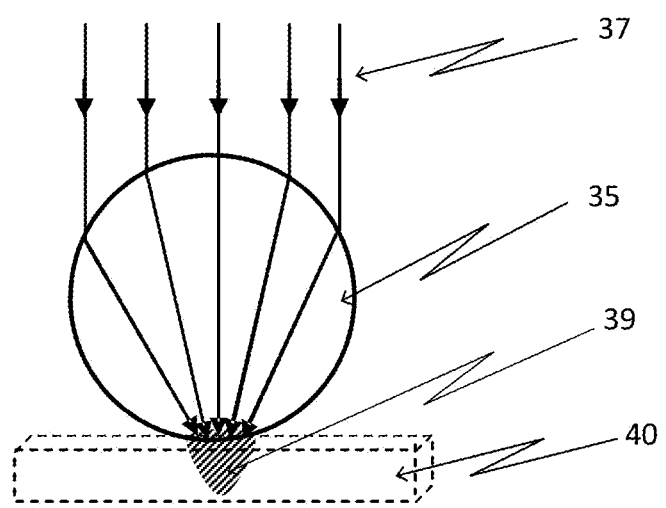
FIG. 3 depicts a microsphere and a produced nanojet according to an embodiment.

One method of increasing the intensity of the impinging light 16 is to focus and confine the light. A Raman scattering signal of a sample may be significantly enhanced by strongly confining the excitation light on the sample. A three dimensional confinement of light is possible by focusing the excitation light with a microsphere. This confinement arises from interferences between the field scattered by the sphere and the incident Gaussian beam containing high angular components. As shown in FIG. 3, a microsphere 35 is able to take an incident beam of radiation 37 and confine the radiation into a photonic nanojet 39. If placed on a sample 40 the more intense nanojet can impinge the sample to increase emissions from the sample. One example of the type of microspheres which may be usable for producing such nanojets are the 9000 series borosilicate glass and soda lime glass microspheres sold by Duke Scientific Corporation.

A photonic nanojet 39 is a narrow, high-intensity, non-evanescent light beam that can propagate over a distance longer than the wavelength λ of the light after emerging from the shadow-side surface of an illuminated lossless dielectric microsphere 35 having a diameter larger than λ. A minimum beamwidth of a nanojet may be smaller than the classical diffraction limit, and may be as small as ~λ/3 for microspheres. A produced nanojet is a non-resonant phenomenon appearing for a wide range of diameters of microspheres if the refractive index contrast relative to the background is less than about 2:1.

A microsphere 35 is able to focus and confine a beam of radiation 37 of several micrometers into a region of few nanometers. By focusing a radiation beam 37 onto a single microsphere 35 disposed on sample 40, the intensity of the resultant Raman emissions may be significantly enhanced. Several factors have been indicated as contributing to the strength of the field in the photonic nanojet. As discussed below, these factors include the pump wavelength of the laser source, the diameter of the microsphere, the relative refractive index of the sphere, and the diameter of the incident radiation beam.

The total electric field in the photonic nanojet emerging from a single dielectric particle due to the plane wave excitation is given by $$E_{jet}(r) = E_{inc}(r) + E_{sca}(r),$$

where r is the radial distance, and $E_{inc}(r)$ and $E_{sca}(r)$, respectively, are the incident and scattered wave fields given by $$E_{inc}(r) = \sum_{n=1}^{\infty} i^n \{(2n+1)/[n(n+1)]\}[M_{o1n}^{(1)}(r) - iN_{e1n}^{(1)}(r)],$$

$$E_{sca}(r) = \sum_{n=1}^{\infty} i^n \{(2n+1)/[n(n+1)]\}[ia_n N_{e1n}^{(3)}(r) - b_n M_{o1n}^{(3)}(r)],$$

where $M_{o\,1n}$ and $N_{e\,1n}$ are the vector spherical harmonics. The superscripts (1) and (3) appended to the vector spherical harmonics denote the spherical Bessel and Hankel functions, respectively. Values $a_n$ and $b_n$ are the scattering coefficients and are the function of the refractive index of the sphere ($n_{sphere}$) relative to the surrounding medium and the size parameter (x). The size parameter is given by $$x = 2\pi a n_{med}/\lambda,$$

where a is the radius of the sphere, λ is the wavelength of the light and $n_{med}$ is the refractive index of the surrounding medium.

In accordance with an embodiment, a microsphere may be configured in conjunction with at least one characteristic of the beam of radiation to confine the beam of radiation in the photonic nanojet by an amount sufficient to enhance the spectroscopic emissions by a factor of at least about 15. The configured microsphere, having a portion for receiving the beam of radiation and outputting a photonic nanojet to impinge the sample, may be placed between the radiation source and the sample, and the beam of radiation may be directed at the microsphere to impinge the beam of radiation on the microsphere and output the photonic nanojet to impinge the sample, excite the sample, and produce the Raman emissions.

At least one microsphere may be placed on the sample surface. Alternatively, several microspheres may be dispersed on the surface. With the aid of magnification, one of the dispersed microspheres may be selected and positioned relative to the radiation source so that the beam of radiation will impinge the selected microsphere and provide an array of spectroscopic emissions. If several microspheres are dispersed on the sample, spectroscopic reading may be obtained from several different locations on the sample.

The beam of radiation has at least two variables which may be altered in conjunction with the microsphere to vary the spectroscopic emissions. One of these variables is the wavelength of the radiation, the other is the dispersion, or light-gathering ability of an objective as quantitatively expressed in terms of the numerical aperture (NA), which is a measure of the number of highly diffracted image-forming light rays captured by the objective. Higher values of numerical aperture allow increasingly oblique rays to enter the objective front lens.

The variables for the configuration of the microsphere include at least the diameter of the microsphere and the refractive index of the microsphere. In one embodiment, by configuring at least one variable of the microsphere in conjunction with at least one of the variable of the radiation, the beam of radiation may be confined in the photonic nanojet by an amount that is sufficient to enhance the spectroscopic emissions by the factor of at least about 15.

In another embodiment, by configuring at least the diameter and the refractive index of the microsphere in conjunction with both the dispersion and the wavelength of the radiation, the beam of radiation may be confined in the photonic nanojet by an amount that is sufficient to enhance the spectroscopic emissions by the factor of at least about 15.

In further embodiments, by configuring at least the diameter and the refractive index of the microsphere in conjunction with both the dispersion and the wavelength of the radiation, the beam of radiation may be confined in the photonic nanojet by an amount that is sufficient to enhance the spectroscopic emissions by a factor of at least about 25, or alternatively, by a factor of at least about 80, depending on materials being tested and the configuration settings as discussed in more detail with the included examples below. Some examples of enhancements which may be attainable with various configurations are about 25, about 30, about 35, about 40, about 45, about 50, about 55, about 60, about 65, about 70, about 80, and any values between any two of these values.

Figures 4A, 4B:
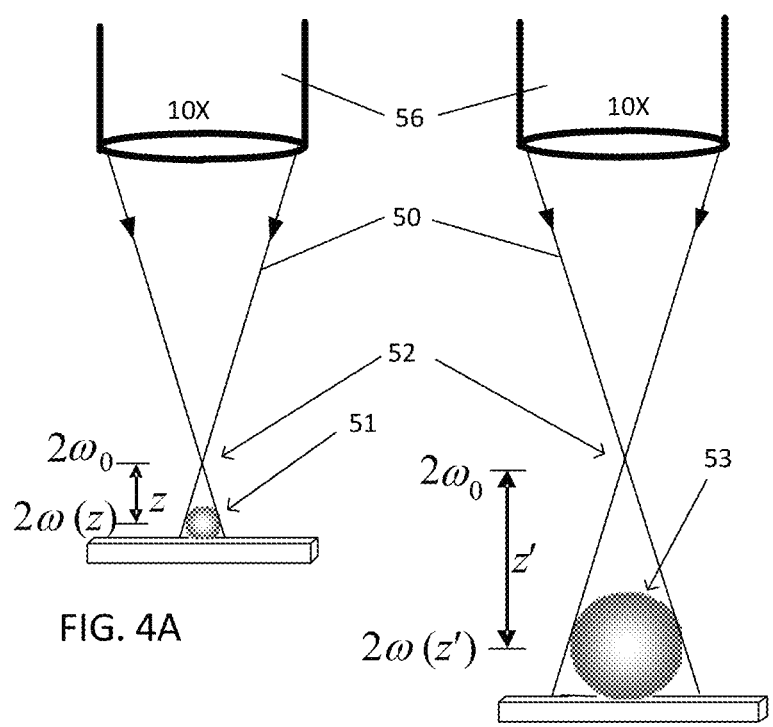
FIGS. 4A and 4B show illustrative representations of microspheres being used in Raman spectroscopy according to embodiments.

As shown in FIGS. 4A and 4B, the dispersion of the radiation 50 and the size of the microsphere (51, 53) may be configured so that the cross-sectional area of the beam of radiation is essentially the same as the diameter of the microsphere. A correspondence of diameters may be obtained by adjusting the numerical aperture, or changing the distance between the microsphere and the radiation source. As shown in FIGS. 4A and 4B, a smaller microsphere 51 may be positioned closer to the source lens 56, at a distance (z) from the focus point 52, than a larger microsphere 53, positioned at a distance (z') from the focus point 52, so that there is a correspondence of the beam diameter with the diameter of the microsphere.

In a beam of radiation, such as a laser beam, the radiation has an effective volume of $(\lambda/n)^3$, wherein λ is a wavelength of the radiation and n is a refractive index of a medium in which the radiation is travelling. The medium for spectroscopy may generally be air. By configuring the microsphere as a function of at least one characteristic of the beam of radiation, the beam of radiation may be confined in three-dimensions to reduce the effective volume of the focused beam to at least about 0.6 $(\lambda/n)^3$. This confinement increases the intensity of the radiation, and when this radiation of increased intensity impinges the sample, a greater number of molecules interact with the available photons. As the number of spectroscopic emissions (photons) are directly related to the intensity, the number of spectroscopic emissions will increase proportionally.

In one embodiment, a microsphere having a diameter of about 30 μm to about 60 μm may provide enhanced emissions. Specific examples of diameters include about 30 μm, about 35 μm, about 40 μm, about 45 μm, about 50 μm, about 55 μm, about 60 μm, and values between any two of these values. In an embodiment, the microsphere may have a refractive index of about 1.56 to about 1.61. Alternatively, the refractive index may be about 1.5602 to about 1.6055. Alternatively, the refractive index may be about 1.56031 to about 1.60425. Some examples of refractive index values include about 1.56031, about 1.56156, about 1.56281, about 1.56406, about 1.56531, about 1.56656, about 1.56781, about, about 1.56906, about 1.57031, about 1.57156, about 1.57281, about 1.57406, about 1.57531, about 1.57656, about 1.57781, about 1.57906, about 1.58031, about 1.58156, about 1.58281, about 1.58406, about 1.58531, about 1.58656, about 1.58781, about 1.58906, about 1.59031, about 1.59156, about 1.59281, about 1.59406, about 1.59531, about 1.59656, about 1.59781, about 1.59906, about 1.60031, about 1.60156, about 1.60281, about 1.60406, about 1.60425 and values between any two of these values. In one embodiment, the refractive index may be about 1.56442. The refractive index for a material will be different for different wavelengths of light, for example, for borosilicate glass spheres the refractive index at various wavelengths may be: 1.60425 at 400 nm, 1.56442 at 632.8 nm and 1.56031 at 700 nm.

In one embodiment, the radiation beam may be a laser beam. In an embodiment, the wavelength of the radiation may be about 400 nm to about 700 nm. Specific examples of radiation wavelengths include about 400 nm, about 420 nm, about 440 nm, about 460 nm, about 480 nm, about 500 nm, about 520 nm, about 540 nm, about 560 nm, about 580 nm, about 600 nm, about 620 nm, about 640 nm, about 660 nm, about 680 nm, about 700 nm, and ranges between any two of these values. In further embodiments, the wavelength may be about 632.8 nm, or alternatively, about 488 nm.

In an embodiment, the numerical aperture for the radiation source may be about 0.20 to about 0.85. Specific examples of numerical apertures include about 0.20, about 0.25, about 0.30, about 0.35, about 0.40, about 0.45, about 0.50, about 0.55, about 0.60, about 0.65, about 0.70, about 0.75, about 0.80, about 0.85, and ranges between any two of these values.

An arrangement for determining parameters for enhanced emissions may include a silicon wafer or $CdTe_2$ thin film as a sample. A silicon wafer has a sharp Raman emission peak at 521 cm$^{-1}$ assigned as the first order transverse optical (TO) mode. The $CdTe_2$ thin film may be deposited on a slide glass from a cadmium telluride (CdTe) bulk by using a thermal evaporation unit (such as that produced by Hind High Vacuum Company, Bangalore, India) at a vacuum of $9 \times 10^{-5}$ mbar. Silica microspheres (such as those from Duke Scientific Corp., Palo Alto, Calif.) and barium titanate ($BaTiO_3$) microspheres (such as those from Mo-Sci. Corp., Rolla, Mo.) may be used as received, and a few microspheres may be dispersed onto the sample surface for spectral measurement.

The Raman spectrum of the silicon wafer or $CdTe_2$ film, may be recorded with a Raman spectrometer (such as the Jobin Yvon, model HR-300) equipped with a He—Ne laser (632.8 nm) and an Ar$^+$ laser (488 nm). The excitation laser with a Gaussian profile may be focused on the substrate through a single microsphere by using a 10×, NA=0.25, microscopic objective lens in a manner as depicted by FIGS. 4A and 4B. The resulting Raman scattering signal may be collected in the backscattering geometry, and may be guided to a CCD detector (such as a Peltier-cooled CCD detector DV420 A-OE-324).

A 3 cm$^{-1}$ resolution (with a grating of 600 grooves/mm) in the Raman shift may be used to record the spectrum. The laser power used to irradiate the sample may be measured at the laser head and may be kept at 20 mW for all the measurements. The exposure time may be kept as 5 seconds for each measurement. The Raman peak of silicon wafer at 521 cm$^{-1}$ may be used to calibrate the spectrometer.

EXAMPLE 1

Effect of Microsphere Diameter

Raman spectra of a silicon wafer prepared as discussed above, were recorded by exciting through single silica microspheres. Without a microsphere, the obtained spectrum was weak as seen by the comparison of the two spectra FIG. 5, Panel A.

With a silica microsphere of a diameter of about 36 μm, the Raman signal was enhanced by a factor of about 16 (calculations are presented further below). This indicated that the electric field is well confined to the surface of the silicon wafer in a nanometer-scale region. Since the Raman scattering signal is strongly dependent on the electric field, the scattering was enhanced due to the strong localization of the electric field. This may be attributed to the photonic nanojet emerging from the single microsphere due to the Gaussian beam excitation. The photonic nanojets may be created with small microspheres having a radius approximately equal to the wavelength of the light, as well as with large microspheres having a radius of approximately 20 times the wavelength of the light.

Figure 5:
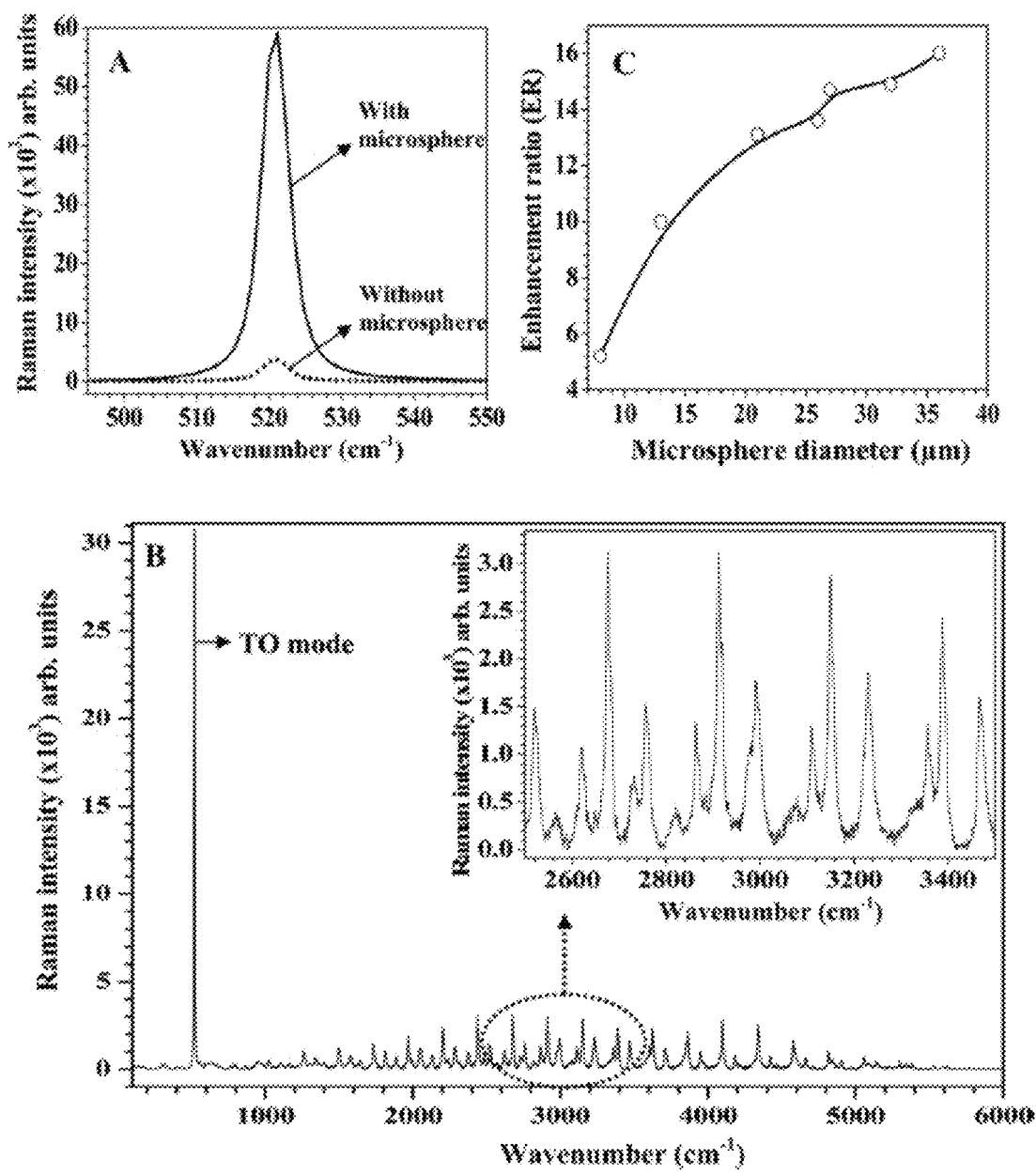
FIG. 5 shows Raman spectra obtained and calculated enhancement ratios according to an embodiment.

The Raman spectrum of a silicon wafer upon excitation through a single silica microsphere having a diameter of about 10 μm is shown in FIG. 5, Panel B. Along with the transverse optical phonon (TO) mode of silicon, several sharp peaks appeared in the lower and higher Raman shift region. These peaks are known as whispering gallery modes (WGMs) of the microsphere.

The value of the enhancement ratio (ER) of the Raman intensity was calculated for different microspheres. This was done by taking the ratio of the Raman intensity of the sample with excitation through a single microsphere (minus the background intensity) to that with the direct excitation without a microsphere (minus the background intensity). The ER was determined to increase with the microsphere diameter as shown in FIG. 5, Panel C. For this data set, the maximum ER (about 16) was obtained for the microsphere of diameter of about 36 μm. This ER was obtained by placing the about 36 μm microsphere at a distance of about 0.11 mm away from the focus point as shown in the FIG. 4A. At this distance, the beam waist can be estimated as follows. The Gaussian beam waist, $\omega(z)$, at a distance (z) is given by $$\omega(z) = \omega_0[1+(\lambda z/\pi\omega_0^2)^2]^{1/2}.$$

where the minimum beam waist, $\omega_0$, at the focus is given by $$\omega_0 = 0.61\lambda/NA.$$

At a distance of 0.11 mm, the beam diameter incident on the microsphere is estimated to be 29.2 μm. The microsphere diameter (36 μm) is within an error of 23% of this estimate. It was also observed that the ER decreased on moving the sample from the focus point toward the objective lens.

EXAMPLE 2

Effect of Refractive Index of the Microsphere

The electric field in the photonic nanojet was also determined to be dependent on the refractive index of the microsphere (equations in paragraph[0023]). To determine the effect of refractive index of the microsphere, the Raman spectra of silicon wafers were recorded by exciting through microspheres of the same size, but of different refractive indexes, a silica microsphere with n=1.56, and a $BaTiO_3$ microsphere a larger refractive index of n=2.1. Table 1 shows the observed values of ER with silica and $BaTiO_3$ microspheres of two different sizes.

TABLE 1

| | ER | |
| --- | --- | --- |
| Diameter (μm) | Silica($n_{sphere}$ = 1.56) | $BaTiO_3$ ($n_{sphere}$ = 2.1) |
| 13 | 10 | 6 |
| 36 | 16 | 14 |

The ER values with the $BaTiO_3$ microspheres are lower than those of silica. This may be attributed to the fact that the electric field strength in the photonic nanojet decreases on increasing the refractive index of the microsphere and is therefore lower in $BaTiO_3$ microsphere.

EXAMPLE 3

Effect of Wavelength of the Impinging Radiation

Along with the refractive index, the electric field in the nanojet was also determined to be dependent upon the pump wavelength of the laser. The Raman spectra of silicon wafers were recorded with excitation radiation of different wavelengths through similar microspheres. Table 2 lists the calculate ER values obtained with the different wavelength radiations.

TABLE 2

| Diameter (μm) | ER | |
|---|---|---|
| | λ = 632.8 nm | λ = 488 nm |
| 13 | 6 | 14 |
| 36 | 14 | 32 |

It was determined that the ER values increase with decreasing λ. This may be attributed to the fact that, in the case of excitation of a dielectric microsphere by a Gaussian beam of wavelength λ, the effective volume of the photonic nanojet beyond the microsphere is given by $$0.6(\lambda/n_{med})^3.$$

Therefore, the photonic nanojet from radiation of λ=488 nm confines into a smaller volume beyond the microsphere as compared to that with radiation of λ=632.8 nm. Due to the stronger confinement of light, the electric field in the photonic nanojet increases more in the case of 488 nm excitation resulting in more enhancement.

EXAMPLE 4

Results with CdTe$_2$ Samples

Figure 6:
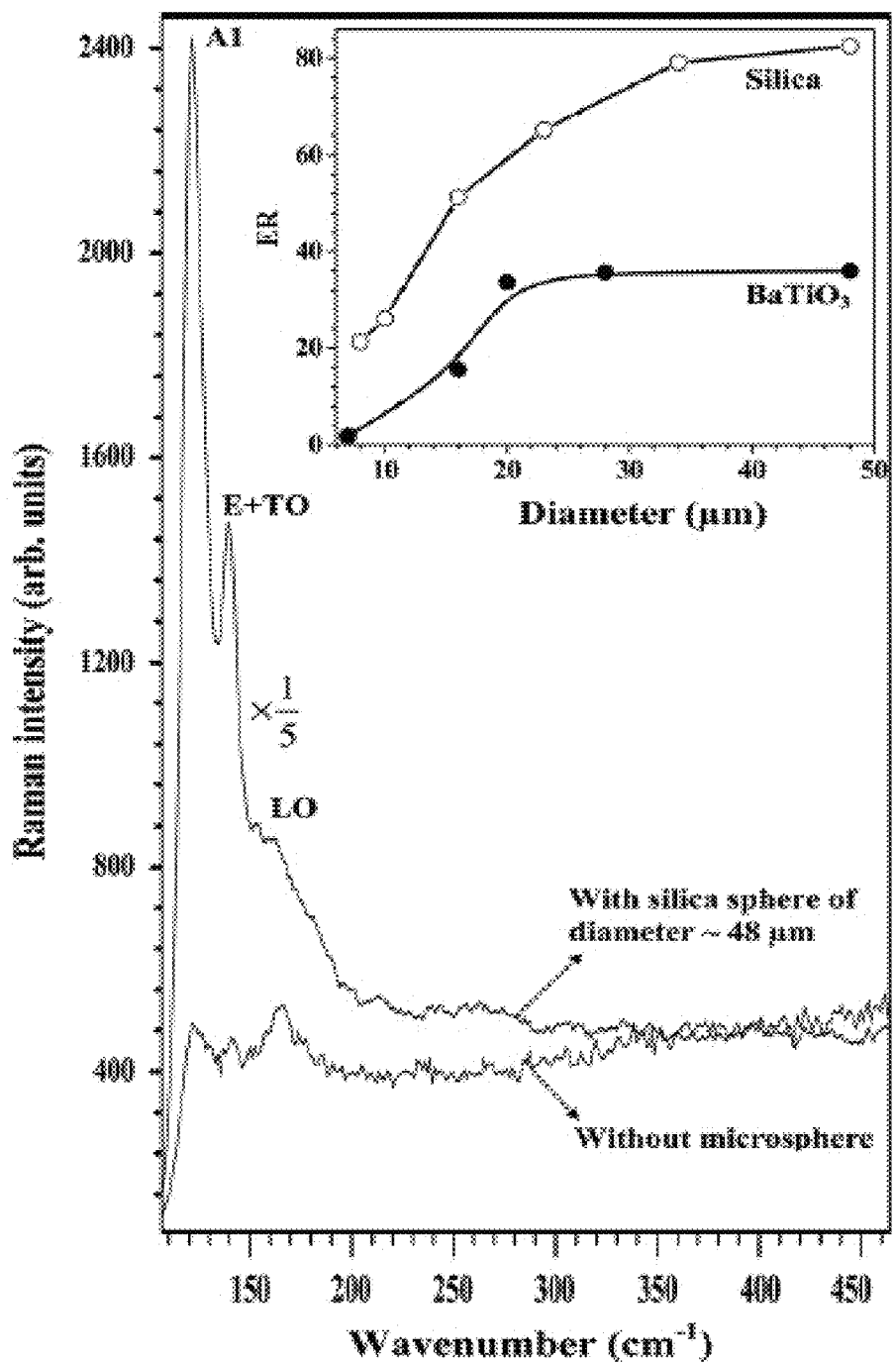
FIG. 6 shows Raman spectra obtained and calculated enhancement ratios according to another embodiment.

To confirm the obtained results from the sample of silicon, a thin film of CdTe$_2$ was also tested. The Raman spectra of the thin film obtained with the excitation wavelength of 632.8 nm are shown in FIG. 6.

For CdTe$_2$, there are three peaks at 123, 141, and 164 cm$^{-1}$ in the spectrum, with the first peak (123 cm$^{-1}$) due to the A1 symmetry phonon (peak labeled as A1). The second peak (141 cm$^{-1}$) is due to both the pure tellurium phase (E) and the transverse optical phonon (TO) of the CdTe lattice (peak labeled as E+TO). The third peak (164 cm$^{-1}$) is the characteristic of the CdTe phase and is due to lattice vibrations along the crystallographic directions—the longitudinal-optical phonon (LO). The intensity of the LO peak obtained with the direct excitation (without microsphere) is higher than that of the remaining peaks. This has been considered as the Raman signature of the CdTe$_2$ phase. The transition takes place from CdTe to CdTe$_2$ phase depending upon the deposition conditions. Upon excitation of the film through the single microsphere, Raman peaks become more intense considerably. However, the enhanced intensity of the LO peak is lower as compared to the other peaks. This may be due to decomposition of the CdTe$_2$ compound into two more stable phases namely CdTe and Te on increasing the incident irradiation power.

The ER values of the A1 peaks obtained with silica and BaTiO$_3$ microspheres are shown in the inset of the above graph. The ER was determined to increase with the microsphere diameter with both types of spheres. However, the observed ER for BaTiO$_3$ microspheres was lower as compared to that with the silica microspheres. The larger silica microsphere (48 μm) gave an ER value of 83 while it was only 35 for the BaTiO$_3$ microsphere of same size. As previously discussed, the lower value of ER is due to the higher refractive index of BaTiO$_3$ microspheres.

EXAMPLE 5

Data and Calculations for the Best Enhancement Achieved

A CdTe$_2$ sample was prepared as discussed above and analyzed with a laser of wavelength 632.8 nm, originating with a numerical aperture of about 0.25. Raman spectra were obtained without a microsphere (FIG. 7A) and with silica microspheres having a refractive index of about 1.56442, and diameters as provided in Table 3. FIG. 7B shows the spectrum obtained with a silica microspheres having a diameter of about 48 μm.

The A1 peak as discussed above was used for comparison. The A1 peak of bare CdTe$_2$ had a value of 525 units in the spectrum of FIG. 7A with a background level of about 402, providing a total peak height of about 123 units. The A1 peak with a 48 μm microsphere had a value of about 12060 units as shown in FIG. 7B with a background intensity of about 1890 units, providing a total peak height of about 10170 units. The enhancement ratio achieved was $$ER = \left(\frac{\text{Peak value} - \text{Background in the each graph}}{\text{Corrected bare intensity from graph 1}}\right) \approx \left(\frac{10107}{123}\right) \approx 83.$$

TABLE 3

| Size of the microsphere (μm) | Peak intensity | Background intensity | Background subtracted peak intensity | ER |
|---|---|---|---|---|
| Without microsphere | 525 | 402 | 123 | 1 |
| 8 | 3560 | 1060 | 2500 | 20 |
| 11 | 3890 | 760 | 3130 | 25 |
| 17 | 7650 | 1495 | 6155 | 50 |
| 23 | 8740 | 890 | 7850 | 64 |
| 34 | 11350 | 1770 | 9580 | 78 |
| 48 | 12060 | 1890 | 10170 | 83 |

This disclosure is not limited to the particular systems, devices and methods described, as these may vary. The terminology used in the description is for the purpose of describing the particular versions or embodiments only, and is not intended to limit the scope.

In the above detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be used, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds, compositions or biological systems, which can, of course, vary. It is also to be understood that the terminology used herein is for the purpose of describing particular embodiments only, and is not intended to be limiting.

As used in this document, the singular forms "a," "an," and "the" include plural references unless the context clearly dictates otherwise. Unless defined otherwise, all technical and scientific terms used herein have the same meanings as commonly understood by one of ordinary skill in the art. Nothing in this disclosure is to be construed as an admission that the embodiments described in this disclosure are not entitled to antedate such disclosure by virtue of prior invention. As used in this document, the term "comprising" means "including, but not limited to."

While various compositions, methods, and devices are described in terms of "comprising" various components or steps (interpreted as meaning "including, but not limited to"), the compositions, methods, and devices can also "consist essentially of" or "consist of" the various components and steps, and such terminology should be interpreted as defining essentially closed-member groups.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

Various of the above-disclosed and other features and functions, or alternatives thereof, may be combined into many other different systems or applications. Various presently unforeseen or unanticipated alternatives, modifications, variations or improvements therein may be subsequently made by those skilled in the art, each of which is also intended to be encompassed by the disclosed embodiments.

What is claimed is:

1. A method for enhancing intensity of Raman emissions produced by excitation of a sample with a laser beam from a laser source, the laser source comprising a lens configured to focus the laser beam to a focal point a first distance from the lens, the laser beam comprising at least one wavelength and having a substantially conical dispersion from the focal point to a distance greater than the first distance, the conical dispersion defining a plurality of diameters increasing in size in a direction away from the focal point, and the method comprising:

placing a microsphere between the radiation source and the sample at a second distance from the lens, the second distance being greater than the first distance, wherein the microsphere comprises a portion for receiving the laser beam and outputting a photonic nanojet to impinge on the sample, and the microsphere has a diameter and a refractive index;

adjusting the second distance in relation to the first distance so that the diameter of the laser beam at the second distance is substantially the same as the diameter of the microsphere, wherein the diameter and refractive index of the microsphere and wavelength of the laser are effective to confine the laser beam in the photonic nanojet by an amount sufficient to enhance the Raman emissions by a factor of at least about 15; and directing the laser beam at the microsphere to impinge the laser beam on the microsphere and output the photonic nanojet to impinge on the sample, excite the sample, and produce the Raman emissions.

2. The method of claim 1, wherein:
the diameter of the microsphere is about 30 µm to about 60 µm;
the refractive index is about 1.56 to about 1.61;
the wavelength is about 400 nm to about 700 nm; and
a numerical aperture of the lens is about 0.25 to about 0.75.

3. A method for enhancing intensity of Raman emissions produced by excitation of a sample with a beam of radiation from a radiation source, the beam of radiation having a dispersion defining a beam diameter along the beam of radiation and also having a focal point a first distance from the radiation source, the method comprising:
placing a microsphere on the sample at a second distance from the radiation source, the second distance being greater than the first distance, the microsphere having a refractive index, a diameter, and a portion for receiving the beam of radiation and outputting a photonic nanojet to impinge the sample, and the radiation source comprising a lens for focusing the beam of radiation;
directing the beam of radiation at the microsphere to impinge the beam of radiation on the microsphere and output the photonic nanojet to impinge the sample, excite the sample, and produce the Raman emissions; and
adjusting the distance between the lens and the microsphere to match the beam diameter of the beam of radiation at the second distance with the diameter of the microsphere,
wherein the diameter and refractive index of the microsphere and at least one wavelength of the beam of radiation are selected in relation to each other to confine the beam of radiation in the photonic nanojet by an amount sufficient to enhance the spectroscopic emissions by a factor of at least about 15.

4. The method of claim 3, wherein:
the lens has a numerical aperture; and
the configuring comprises selecting the diameter and the refractive index of the microsphere in accordance with the numerical aperture of the lens and the at least one wavelength of the beam of radiation to match the diameter of the beam of radiation at the second distance with the diameter of the microsphere and confine the beam of radiation in the photonic nanojet by an amount sufficient to enhance the spectroscopic emissions by a factor of at least about 15.

5. The method of claim 4, wherein the beam of radiation is confined into the photonic nanojet by an amount sufficient to enhance the spectroscopic emissions by a factor of at least about 25.

6. The method of claim 4, wherein the beam of radiation is confined into the photonic nanojet by an amount sufficient to enhance the spectroscopic emissions by a factor of at least about 80.

7. The method of claim 3, wherein:
the beam of radiation has an effective volume of $(\lambda/\eta)^3$, wherein $\lambda$ is a wavelength of the radiation and $\eta$ is a refractive index of a medium in which the radiation is travelling; and
the configuring comprises selecting the diameter and the refractive index of the microsphere in accordance with the numerical aperture of the lens and the at least one wavelength of the beam of radiation to confine the beam of radiation in three-dimensions to reduce the effective volume of the focused beam to at least about $0.6\,(\lambda/\eta)^3$.

8. The method of claim 3, wherein the microsphere has a diameter of at least about 30 µm.

9. The method of claim 3, wherein the microsphere comprises a silica microsphere.

10. The method of claim 3, wherein:
the placing of the microsphere comprises placing at least one microsphere on a surface of the sample; and
the directing of the beam of radiation comprises selecting one of the at least one microspheres on the surface of the sample and directing the beam of radiation at the selected one of the microspheres.

11. The method of claim 3, wherein the beam of radiation comprises a laser beam.

12. The method of claim 3, wherein:
the beam of radiation comprises a laser beam;
the microsphere comprises a silica microsphere having a cross-sectional area defined by the diameter of the microsphere, and a hemisphere disposed towards the radiation source to receive the beam of radiation, the hemisphere defining the radiation receiving portion; and
the method further comprises adjusting the distance between the lens and the microsphere so that the cross-sectional area of the laser beam at the receiving hemisphere is substantially the same as the cross-sectional area of the microsphere.

13. The method of claim 3, wherein:
the beam of radiation comprises a laser beam;
the lens focuses the laser beam to the focal point at the first distance from the lens;
the laser beam has a substantially conical dispersion from the focal point to a distance greater than the first distance, the conical dispersion defining a plurality of diameters increasing in size in a direction away from the focal point; and
the method further comprises adjusting the second distance in relation to the first distance so that the diameter of the laser beam at the second distance is substantially the same as the diameter of the microsphere.

14. The method of claim 13, wherein:
the radiation source comprises a lens having a numerical aperture of about 0.25 to about 0.75;
the diameter of the microsphere is about 30 µm to about 60 µm;
the microsphere has a refractive index of about 1.56 to about 1.61; and
the laser beam has a wavelength of about 400 nm to about 700 nm.

15. The method of claim 13, wherein:
the radiation source comprises a lens having a numerical aperture of about 0.75;
the diameter of the microsphere is about 36 µm;
the microsphere comprises a silica sphere having a refractive index of about 1.56442; and
the beam of radiation has a wavelength of about 632.8 nm.

16. The method of claim 15, wherein the sample is a silicon wafer.

17. The method of claim 13, wherein:
the radiation source comprises a lens having a numerical aperture of about 0.75;
the diameter of the sphere is about 48 µm;
the sphere comprises a silica sphere having a refractive index of about 1.56442;
the beam of radiation has a wavelength of about 632.8 nm; and the Raman scattering emissions are enhanced by a factor of at least about 80.

18. The method of claim 3, wherein the sample is cadmium ditelluride.

19. The method of claim 3, wherein the sample comprises a pharmaceutical drug, a composite, a polymer, a gem, a semiconductor, a carbon compound, a biological tissue, and thin film photovoltaics.

20. A method for analyzing a sample by Raman spectroscopy, the method comprising:
placing the sample in a spectrometer, the spectrometer comprising:
a laser source for producing a laser beam of radiation to impinge the sample and produce Raman emissions from the sample, the laser source comprising a lens to focus the laser beam to a focal point a first distance from the lens, the laser beam having at least one wavelength and a substantially conical dispersion from the focal point to a distance greater than the first distance, the conical dispersion defining a plurality of diameters increasing in size in a direction away from the focal point; and
a detector for receiving the Raman emissions;
placing at least one microsphere on a surface of the sample at a second distance from the lens, the second distance being greater than the first distance, the microsphere having a refractive index, a diameter, and a portion for receiving the laser beam, confining the laser beam and outputting a photonic nanojet to impinge the sample;
directing the laser beam at one of the at least one microspheres;
adjusting a distance of the sample from the laser source so that the diameter of the laser beam at the microsphere is substantially the same as the diameter of the microsphere; and
detecting the Raman emissions produced by the photonic nanojet;
wherein the refractive index of the microsphere, the diameter of the microsphere, and at least one wavelength of the laser beam are selected in relation to each other to confine the laser beam in the photonic nanojet by an amount sufficient to enhance the Raman emissions by a factor of at least about 15.

21. The method of claim 20, wherein the diameter and the refractive index of the microsphere and the wavelength of the laser beam confine the laser beam into the photonic nanojet by an amount sufficient to enhance the spectroscopic emissions by a factor of at least about 25.

22. The method of claim 20, wherein the diameter and the refractive index of the microsphere and the wavelength of the laser beam confine the laser beam into the photonic nanojet by an amount sufficient to enhance the spectroscopic emissions by a factor of at least about 80.

23. The method of claim 20, wherein:
the laser beam has an effective volume of $(\lambda/\eta)^3$, wherein $\lambda$ is a wavelength of the laser beam and $\eta$ is a refractive index of a medium in which the laser beam is travelling; and
the microsphere is configured to confine the laser beam in three-dimensions to reduce the effective volume of the laser beam to at least about $0.6\ (\lambda/\eta)^3$.

24. The method of claim 20, wherein the microsphere has a diameter of at least about 30 μm.

25. The method of claim 20, wherein the microsphere comprises a silica microsphere.

26. The method of claim 20, wherein the laser beam has a wavelength of about 400 nm to about 700 nm.

27. The method of claim 20, wherein:
the radiation source comprises a lens having a numerical aperture of about 0.25 to about 0.75;
the diameter of the microsphere is about 30 μm to about 60 μm;
the microsphere comprises a silica microsphere having a refractive index of about 1.56 to about 1.61; and
the beam of radiation has a wavelength of about 400 nm to about 700 nm.

28. The method of claim 20, wherein:
the radiation source comprises a lens having a numerical aperture of about 10;
the diameter of the microsphere is about 36 μm;
the microsphere comprises a silica microsphere having a refractive index of about 1.56442; and
the beam of radiation has a wavelength of about 632.8 nm.

29. The method of claim 28, wherein the sample is a silicon wafer.

30. The method of claim 20, wherein:
the radiation source comprises a lens having a numerical aperture of about 10;
the diameter of the microsphere is about 48 μm;
the microsphere comprises a silica microsphere having a refractive index of about 1.56442;
the beam of radiation has a wavelength of about 632.8 nm; and
the Raman emissions are enhanced by a factor of at least about 80.

31. The method of claim 30, wherein the sample is a cadmium ditelluride thin film.

32. The method of claim 20, wherein the sample comprises a pharmaceutical drug, a composite, a polymer, a gem, a semiconductor, a carbon compound, a biological tissue, and a thin film photovoltaic.

* * * * *

UNITED STATES PATENT AND TRADEMARK OFFICE
CERTIFICATE OF CORRECTION

PATENT NO. : 9,170,203 B2  
APPLICATION NO. : 13/472987  
DATED : October 27, 2015  
INVENTOR(S) : Bisht et al.

Page 1 of 1

It is certified that error appears in the above-identified patent and that said Letters Patent is hereby corrected as shown below:

IN THE DRAWINGS

Figure 7A:
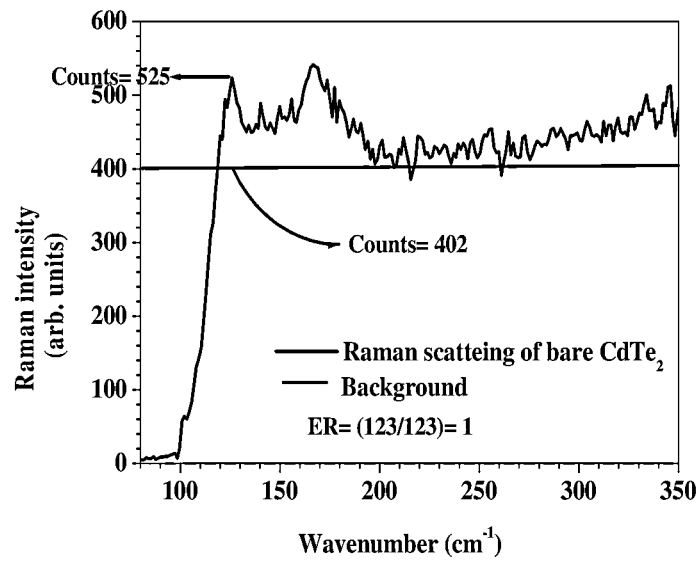
FIGS. 7A and 7B show Raman spectra obtained according to an additional embodiment.
Figure 7B:
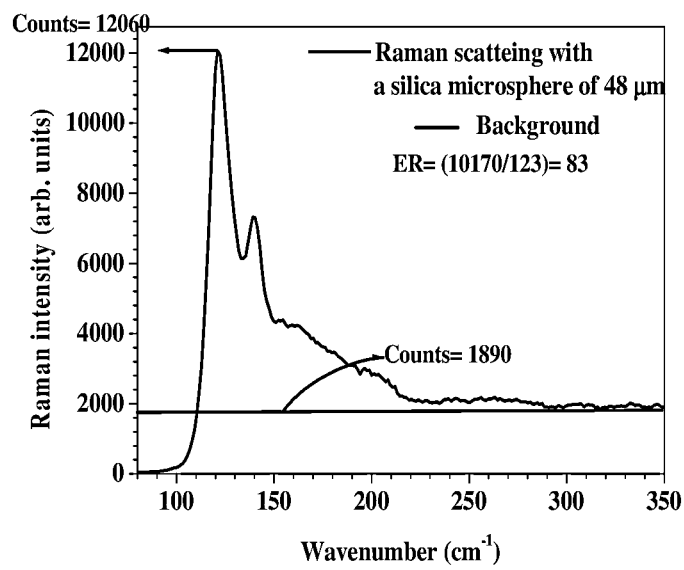

In Fig. 7A, Sheet 6 of 6, delete "Raman scatteing" and insert -- Raman scattering --, therefor.

In Fig. 7B, Sheet 6 of 6, delete "Raman scatteing" and insert -- Raman scattering --, therefor.

IN THE SPECIFICATION

In Column 6, Line 40, delete "1.56781, about," and insert -- 1.56781, --, therefor.

Signed and Sealed this  
Eighth Day of March, 2016

Michelle K. Lee  
*Director of the United States Patent and Trademark Office*